United States Patent [19]

Natwick et al.

[11] Patent Number: 5,039,279
[45] Date of Patent: Aug. 13, 1991

[54] SENSOR FOR DETECTING FLUID FLOW FROM A POSITIVE DISPLACEMENT PUMP

[75] Inventors: Vernon R. Natwick, Los Altos; Michael W. Lawless, Boulder Creek, both of Calif.

[73] Assignee: Abbott Laboratories, Abbott Park, Ill.

[21] Appl. No.: 494,201

[22] Filed: Mar. 15, 1990

[51] Int. Cl.$^5$ ............................................. F04B 49/10
[52] U.S. Cl. ..................................... 417/63; 417/474; 417/479
[58] Field of Search ............ 417/44, 63, 474, 479; 137/554; 116/264, 266, 277

[56] References Cited

U.S. PATENT DOCUMENTS

| | | | |
|---|---|---|---|
| 2,412,397 | 12/1946 | Harper . | |
| 3,609,069 | 9/1971 | Martinelli | 417/474 |
| 4,236,880 | 12/1980 | Archibald | 417/479 |
| 4,277,226 | 7/1981 | Archibald | 417/38 |
| 4,302,164 | 11/1981 | Manella | 417/474 |
| 4,322,201 | 3/1982 | Archibald | 417/279 |
| 4,373,525 | 2/1983 | Kobayashi | 417/474 X |
| 4,391,600 | 7/1983 | Archibald | 604/153 |
| 4,479,797 | 10/1984 | Kobayashi et al. | 604/153 |
| 4,559,038 | 12/1985 | Berg et al. | 604/153 |
| 4,650,469 | 3/1987 | Berg et al. | 604/131 |
| 4,653,987 | 3/1987 | Tsuji et al. | 417/360 |
| 4,690,673 | 9/1987 | Bloomquist | 604/67 |
| 4,728,265 | 3/1988 | Cannon | 417/363 |
| 4,818,186 | 4/1989 | Pastrone et al. | 417/63 |
| 4,836,752 | 6/1989 | Burkett | 417/474 X |
| 4,872,813 | 10/1989 | Gorton et al. | 417/479 X |
| 4,967,940 | 11/1990 | Blette et al. | 417/474 X |

Primary Examiner—Leonard E. Smith
Assistant Examiner—Eugene L. Szczecina, Jr.
Attorney, Agent, or Firm—Christensen, O'Connor, Johnson & Kindness

[57] ABSTRACT

A flow detector for use in a volumetric pump to determine if fluid is being displaced by the pump. The volumetric pump (30) includes an inlet cracking valve (46) and an outlet cracking valve (52) disposed on opposite sides of a plunger (48) used to displace fluid by compressing flexible tubing (34). During a pumping segment of a pumping cycle for the volumetric pump, the outlet cracking valve is closed with a cracking force that compresses the flexible tubing until the pressure of the fluid displaced by the plunger exceeds a cracking pressure, at which time the outlet cracking valve opens to enable fluid flow from the volumetric pump. A cracking flexure (182) provides the cracking force. As the outlet cracking valve opens in response to the fluid passage exceeding the cracking pressure, a flow detector (54) comprising in one preferred embodiment a strain gauge (198) mounted to the cracking flexure responds to the stress generated in the cracking flexure thereby, producing a signal indicative of fluid flow from the volumetric pump. Other types of sensors, including an optical sensor (300), and a linear variable displacement transformer (LVDT) (318) are alternatively used for sensing movement of an outlet valve arm (180) as fluid flows from volumetric pump (30). Since a compressible gaseous fluid in the pumping portion of the flexible tubing does not develop the cracking pressure, the flow detector also provides an indication when a source of liquid (31) for the volumetric pump has run dry.

22 Claims, 10 Drawing Sheets

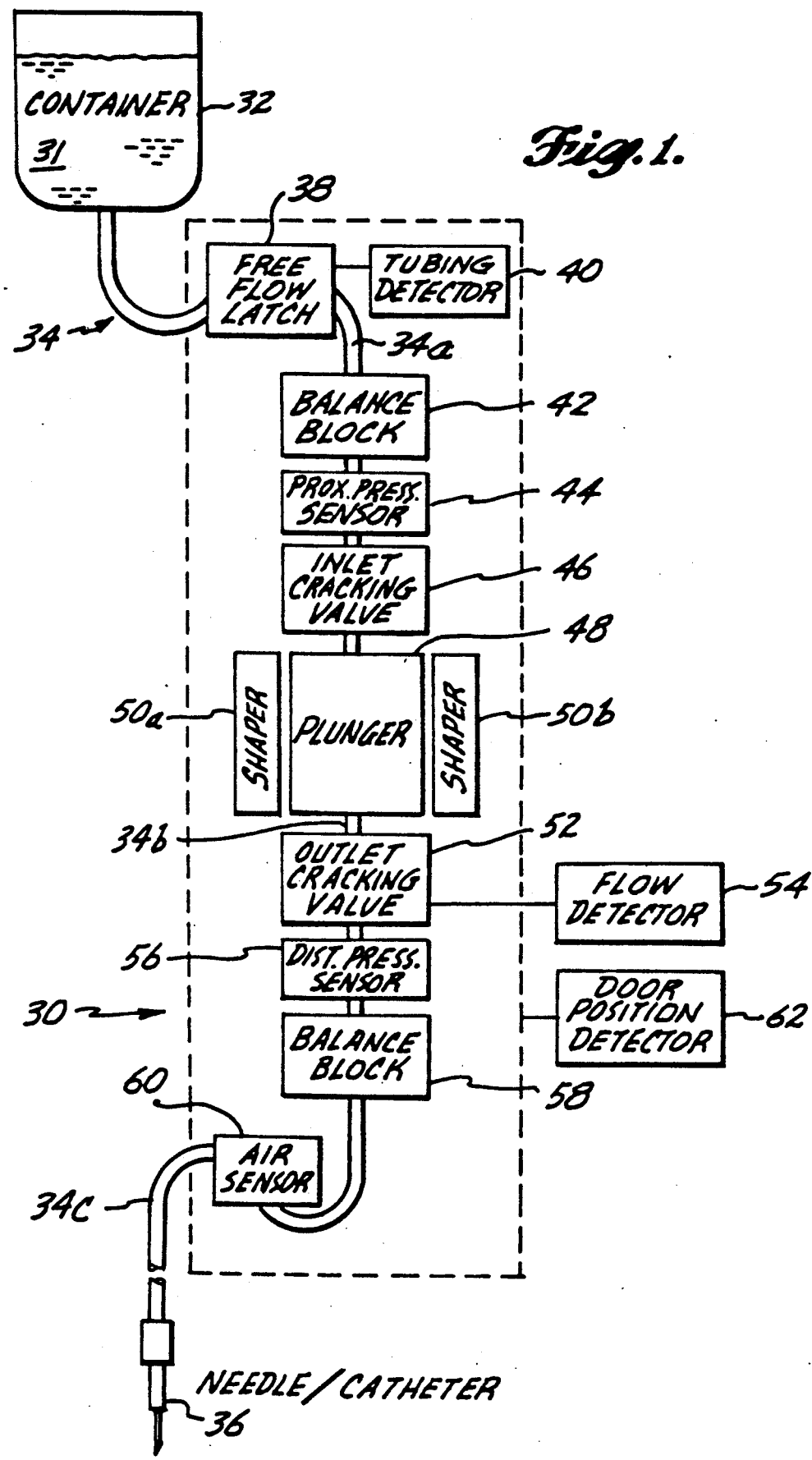

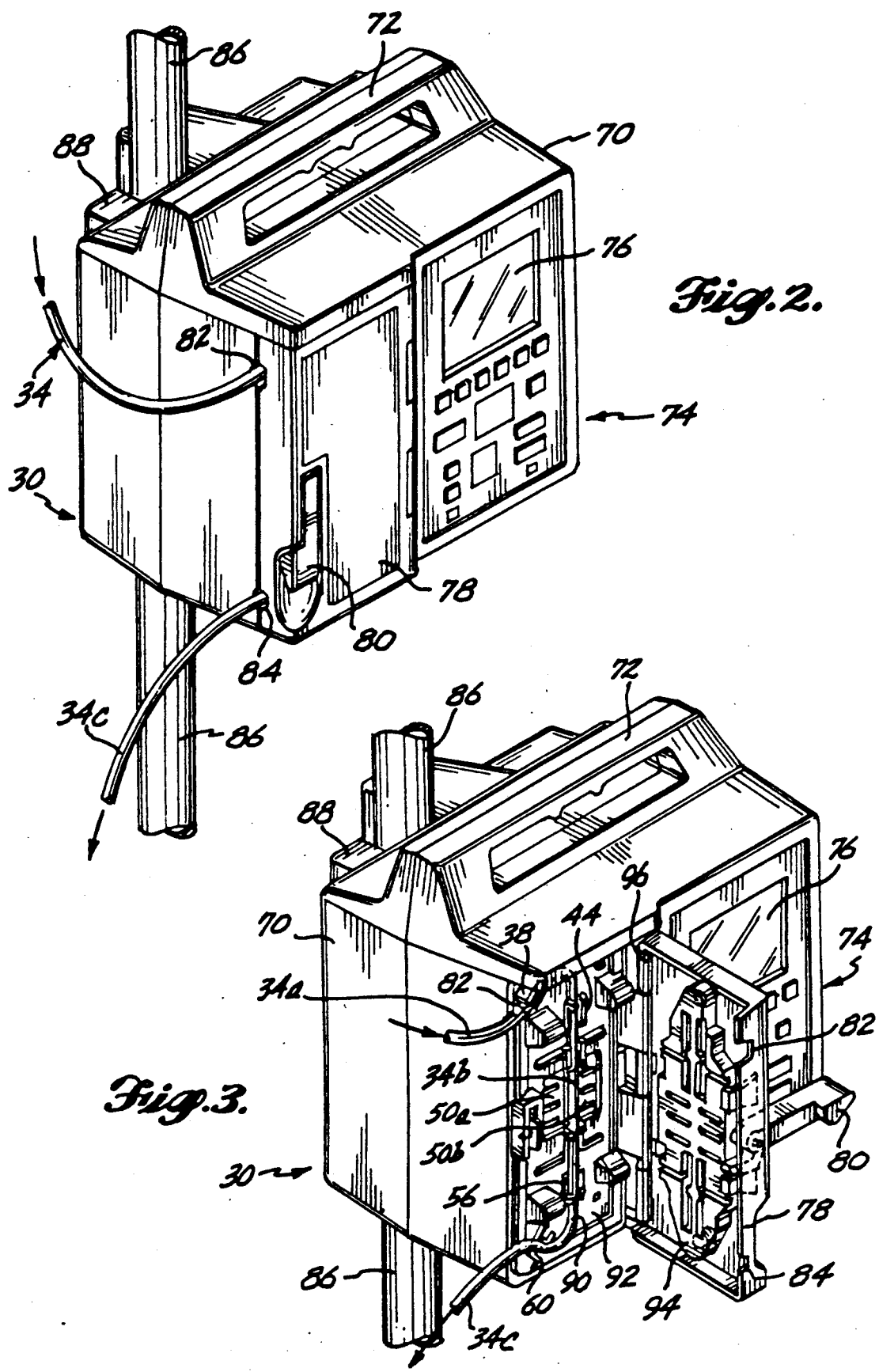

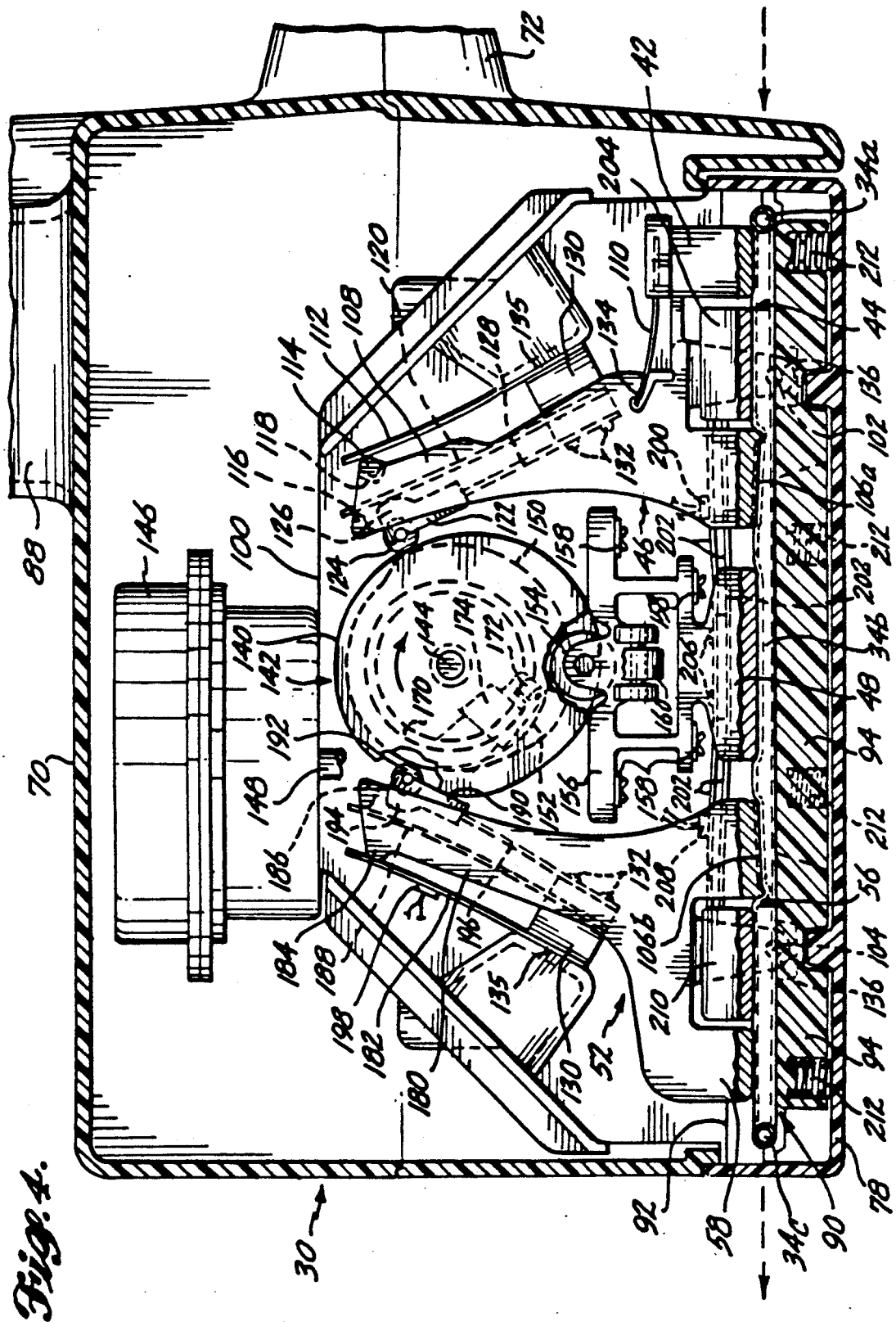

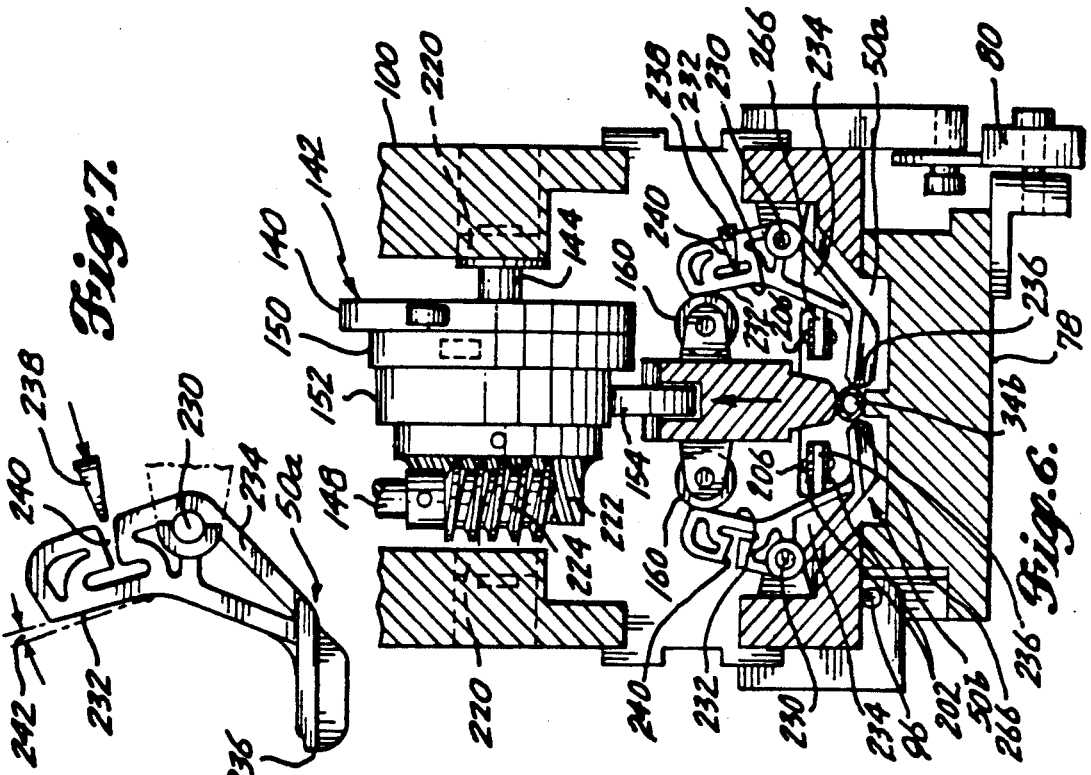
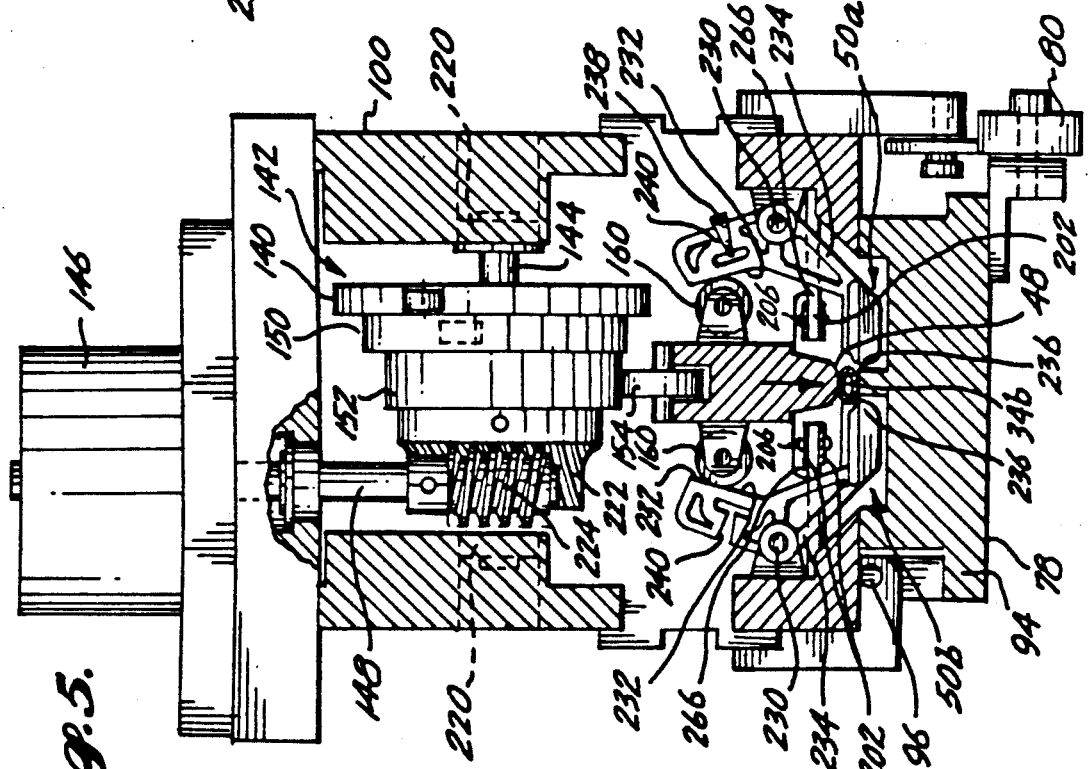

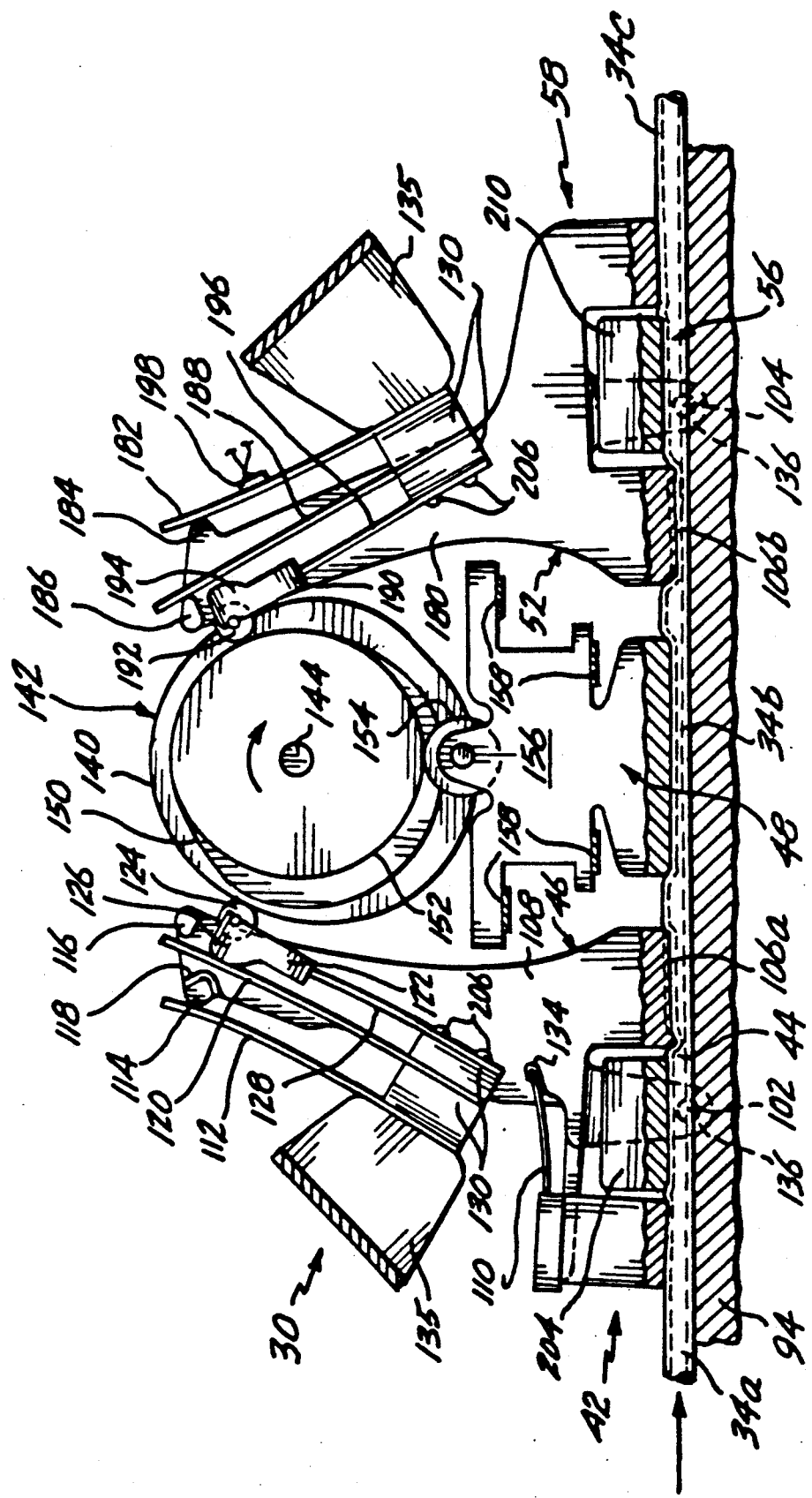

SENSOR FOR DETECTING FLUID FLOW FROM A POSITIVE DISPLACEMENT PUMP

TECHNICAL FIELD

This invention generally pertains to a sensor for monitoring the operation of a pump, and more specifically, to apparatus for monitoring a fluid flow condition related to the operation of a positive displacement pump.

BACKGROUND OF THE INVENTION

One of the important safety concerns that arises in the use of a pump to intravenously administer drugs to a patient is the need to insure that the medication is reaching the patient at the desired rate. Although medical personnel properly set the controls of an infusion pump to supply medication to the patient at the prescribed rate, the lines to and from the pump may become kinked or otherwise obstructed, for example, due to the patient rolling over onto a line. Many drug infusion pumps have fail-safe mechanisms to prevent drugs from being delivered to a patient at an excessive (e.g., free flow) rate, but only a few are provided with means for detecting a blockage in the delivery or supply lines. Pumps that detect an obstruction in the delivery line usually monitor pressure at the pump output port. Blockage of fluid flow from the pump is detected when the pressure at the pump output port increases to a level that exceeds a predetermined threshold. For detecting an obstruction of the supply line that leads from the drug container to the pump, or for detecting that the drug container is empty, some pumps use drip detectors installed in the supply line immediately upstream of the pump inlet. However, connection of the drip detector adds to the time required to set up a drug infusion system, requires additional hardware, and makes the system more complex to use.

Another potential problem with this type of system concerns the infusion of excessive amounts of air into the patient's circulatory system. To prevent this condition, some infusion pumps include an air-in-line sensor that detects air bubbles larger than a specified size, e.g. larger than 100 microliters, since such bubbles can produce an air embolism in the patient's circulatory system that may be harmful. Air-in-line detectors typically monitor the fluid output of the pump using a matched resonant frequency ultrasonic piezoelectric transmitter and receiver that are disposed on opposite sides of a fluid passage in the pump. The ultrasonic piezoelectric transmitter applies an ultrasonic signal to one side of the fluid passage and the receiver monitors the level of that signal on the other side of the passage. Air bubbles in the fluid passage larger than the prescribed maximum size attenuate the ultrasonic signal that reaches the receiver, causing its output signal to fall below a predefined minimum level. A pump control circuit responds to the reduced output signal level caused by a large air bubble and shuts the pump off to prevent the air bubble from being infused into the patient. Additionally, an alarm is sounded to alert medical personnel that the pump has ceased operation, so that the problem causing the air bubbles can be corrected and operation of the pump restored to normal.

In addition to detecting air bubbles larger than a predefined size in the fluid administered using an infusion pump, an air-in-line sensor should ideally monitor the percentage of air being infused in the fluid, since many smaller air bubbles can coalesce to form a dangerous air embolism in the patient's circulatory system. For example, if the air-in-line sensor detects that more than ten (10) percent of the infused fluid comprises air, the pump should be stopped and an alarm sounded so that the condition causing the small air bubbles can be corrected. However, air-in-line sensors that must be calibrated to respond to a wide range of air bubble sizes are more likely to produce false alarms and to be less accurate in determining the percentage of air infused in the form of small bubbles. It would be preferable to use a different mechanism to prevent relatively larger volumes of air from being infused into a patient.

In consideration of each of the above-described problems, it is an object of this invention to detect whether fluid is flowing through a positive displacement pump. It is a further object to use a sensor integral to the pump to detect that a supply container for the fluid is empty, or to detect that a supply line from the container is blocked, preventing the fluid reaching the inlet of the pump. Yet a further object is to detect the presence of a substantial volume of air or other gaseous fluid in a pumping chamber of the pump and prevent the volume of gaseous fluid being forced from the pump. A still further object is to provide an alarm if the pump is operating, but is not pumping fluid from the pumping chamber. These and other objects and advantages of the present invention will become apparent from the attached drawings and the Description of the Preferred Embodiments that follows.

SUMMARY OF THE INVENTION

In accordance with this invention, apparatus for sensing fluid flow through a passage defined by a flexible member in a positive displacement pump is defined. The apparatus includes a valve member that is mounted in the pump, pivots around a pivot axis, and has a surface that engages the flexible member. A spring is mounted in biasing relationship to the valve member, causing the valve member to compress a portion of the flexible member with a "cracking force" and restrict fluid flow through the passage. Fluid pressure in the passage in excess of a predetermined "cracking pressure" produces a force that opposes the cracking force developed by the spring, forcing open the valve member, and enabling fluid to flow through the passage past the valve member. Flow detector means mounted proximal the spring are operative to produce a signal indicative of a deflection experienced by the valve member due to fluid pressure acting on the valve member in opposition to the cracking force developed by the spring. Control means are connected to receive the signal produced by the flow detector means and to determine whether fluid is flowing past the valve member within the passage as function of the signal.

If the pump is attempting to positively displace a gaseous fluid in the passage (in contrast to a liquid), the fluid pressure developed is less than the cracking pressure and thus insufficient to enable the gaseous fluid to flow past the valve member in the passage. Thus, as a function of the signal indicative of the spring deflection, the control means are operative to determine whether the pump is compressing a gaseous fluid or positively displacing a liquid.

Preferably, the flexible member is flexible tubing through which fluid flows within the pump. The valve member compresses the flexible tubing against a backing surface on the pump to restrict fluid flow through the pump past the valve member. The spring preferably comprises an elongate flat flexure that is mounted at one point along its length to the pump and extends therefrom into abutting contact with the valve member. The valve member includes a surface against which the flexure abuts to apply the force that biases the valve member to compress the flexible member. Disposed between the point where the flexure is mounted to the pump and a point where the flexure abuts against the surface of the valve member is the detector means. The control means determine that a fluid is flowing past the valve member if a magnitude of the signal produced by the flow detector means exceeds a predetermined level. Alternatively, the flow detector means can comprise a strain gauge, an optical sensor, a Hall sensor, or a variable reactance sensor (i.e., a linear variable displacement transformer or a variable capacitor sensor).

BRIEF DESCRIPTION OF THE DRAWINGS

FIG. 1 is a schematic block diagram of a volumetric pump in which the present invention is used;

FIG. 2 is an isometric view of the volumetric pump, showing an access door that is closed and latched in place;

FIG. 3 is an isometric view, similar to that shown in FIG. 2, but with the access door shown in an open position, disclosing the path followed by flexible tubing through the volumetric pump;

FIG. 4 is a longitudinal cross section of the pump assembly shown in FIGS. 2 and 3;

FIG. 5 is a schematic transverse cross section of the volumetric pump, illustrating compression of the flexible tubing to pump fluid;

FIG. 6 is a schematic cross section of the volumetric pump, illustrating reshaping of the flexible tubing to facilitate its filling with fluid;

FIG. 7 is a plan view illustrating the calibration of one of the tube reshaping arms to achieve a desired angular deflection;

FIGS. 10A-10C are cutaway, longitudinal cross sections of the volumetric pump respectively illustrating a fill segment, a pumpback-pressurization segment, and a pumping segment of its pumping cycle;

DESCRIPTION OF THE PREFERRED EMBODIMENTS

Figure 8:
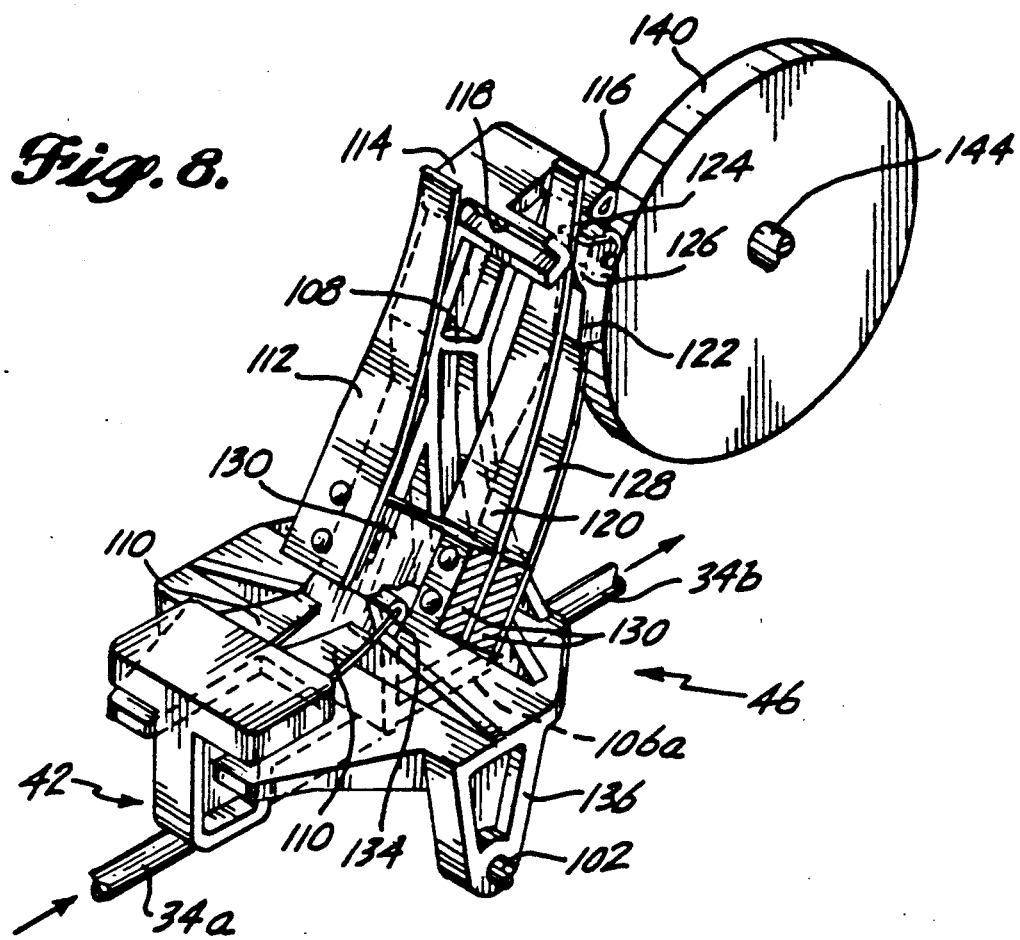
FIG. 8 is an isometric view of an inlet cracking valve used in the volumetric pump and a transverse section of a cam assembly that is used to actuate the cracking valve.

The term "volumetric pump" is used in connection with a positive displacement pump with which the present invention is used because it appropriately emphasizes one of the more important advantages of this pump. Specifically, during each pumping stroke, the volumetric pump consistently and repeatedly displaces a defined volume of fluid at a defined pressure, thereby ensuring that a desired rate of fluid flow is accurately provided by the pump. The present invention is used with the volumetric pump to monitor its operation and to provide an alarm in the event that fluid flow from the volumetric pump is interrupted.

In FIG. 1, a volumetric pump in accordance with the present invention is generally illustrated in block diagram at reference numeral 30. Volumetric pump 30 comprises a number of components that are serially arranged along a fluid path through the pump. A liquid 31 that is administered by volumetric pump 30 is supplied from a container 32 through flexible tubing 34. Liquid 31 enters volumetric pump 30 through a proximal portion 34a of the flexible tubing. The fluid path continues through a pumping portion 34b and exits the pump through a distal portion 34c of the flexible tubing. Distal portion 34c of the flexible tubing is connected to a needle/catheter 36 that is used to introduce liquid 31 output from the pump intravenously into a patient. Of course, volumetric pump 30 may also be used in other applications wherein distal portion 34c of the flexible tubing is connected to some other apparatus disposed downstream of volumetric pump 30.

Flexible tubing 34 is continuous, but for purposes of this disclosure, is referred to as divided into the proximal, pumping, and distal portions 34a, 34b, and 34c, respectively; preferably, it comprises a polyvinyl chloride (PVC) disposable tube set, such as is customarily used to administer fluids intravenously to a patient. The tubing may have a 0.137" O.D. and 0.100" I.D.

In this application of the volumetric pump, it is desirable to prevent free flow of liquid 31 from container 32 into the patient. For this reason, volumetric pump 30 includes a free flow latch 38, which clamps proximal portion 34a of the flexible tubing to prevent liquid 31 from container 32 flowing freely into a patient, due to head pressure. Free flow latch 38 does not restrict fluid flow during the normal pumping operation of volumetric pump 30, but is configured to automatically clamp proximal portion 34a of the flexible tubing when a door 78 (shown in FIGS. 2 and 3) on volumetric pump 30 is opened. While door 78 is closed, free fluid flow through volumetric pump 30 is otherwise precluded by volumetric pump 30, as explained below. The position of door 78 is sensed by a door position detector 62, producing a signal that prevents operation of volumetric pump 30 when door 78 is open. Similarly, a tubing detector 40 is interconnected to free flow latch 38, and produces a signal indicative of the presence of flexible tubing 34 within free flow latch 38; operation of volumetric pump 30 inhibited if the signal indicates that the flexible tubing is not in place.

A balance block 42 rests against proximal portion 34a of flexible tubing 34 and serves to compensate for variations or changes in the elastcity of flexible tubing 34. The function and operation of balance block 42 are more fully explained below.

Next in the serial arrangement of components along the fluid path within volumetric pump 30 is a proximal pressure sensor 44, which operates to sense the pressure of fluid within proximal portion 34a of the flexible tubing. Proximal pressure sensor 44 produces a signal indicative of fluid pressure in this portion of flexible tubing 34 for use in monitoring the operation of the pump and to determine if proximal portion 34a has become occluded.

An inlet cracking valve 46 is disposed immediately downstream of proximal pressure sensor 44. Inlet cracking valve 46 functions in cooperation with a plunger 48 and an outlet cracking valve 52, which are disposed sequentially downstream of the inlet cracking valve, to provide the displacement of a volumetric quantity of fluid from pumping portion 34b of the flexible tubing by volumetric pump 30 and to generally isolate the volumetric pump from variations in proximal and distal fluid pressure, due, for example, to variations in the elevation of container 32, or variations in the back pressure of fluid in distal portion 34c of the flexible tubing. Tubing shapers 50a and 50b are disposed at each side of plunger 48 and act to rapidly reform pumping portion 34b of the flexible tubing as it refills with fluid during each pump cycle, insuring consistent volumetric refill with each pumping stroke.

A flow detector 54 in accordance with the present invention is functionally connected with outlet cracking valve 52. Flow detector 54 produces a signal indicating whether fluid is successfully being pumped by volumetric pump 30 into distal portion 34c of the flexible tubing. As explained below, in response to this signal, medical personnel are alerted if container 31 has become empty of liquid 31 or if any other problem has prevented fluid flow from volumetric pump 30.

A distal pressure sensor 56 produces a signal indicative of the fluid pressure within distal portion 34c of the flexible tubing, i.e., the output pressure of volumetric pump 30. The distal fluid pressure is used for monitoring the operation of volumetric pump 30 and for sensing an occlusion of flexible tubing 34.

Immediately adjacent distal pressure sensor 56 is a balance block 58. Cooperating with outlet cracking valve 52, a balance block 58 compensates for changes or variations in the stiffness or elasticity of flexible tubing 34, in a manner similar to that in which balance block 42 cooperates with inlet cracking valve 46.

An air sensor 60 is the last component along the fluid path through volumetric pump 30. Air sensor 60 detects the presence of air bubbles larger than a predefined volume in the fluid discharged from the volumetric pump, and produces a signal indicative of such air bubbles, which stops volumetric pump 30 and initiates an alarm to prevent a potentially harmful air embolism forming in the fluid being introduced into a patient through needle/catheter 36. Air sensor 60 comprises a generally conventional piezoelectric ultrasonic transmitter and receiver (not separately shown), spaced apart on opposite sides of distal portion 34c of the flexible tubing. The transmitter produces an ultrasonic signal that is transmitted through flexible tubing 34 to the receiver. Liquid present in flexible tubing 34 between the transmitter and receiver conveys the ultrasonic signal much more efficiently than does an air bubble. The receiver produces an electronic signal in response to the level of the ultrasonic signal reaching it, the amplitude of the electronic signal indicating whether an air bubble or liquid is present in flexible tubing 34 between the transmitter and receiver. Details of air sensor 60 are not illustrated because such devices are generally well known to those of ordinary skill in this art.

Proximal pressure sensor 44, distal pressure sensor 56, air sensor 60, and flow detector 54 form a complete monitoring system to ensure that volumetric pump 30 is operating properly. To some extent, these components have redundant functions, but flow detector 54 serves as a final back-up for the monitoring system, since it detects whether the volumetric pump is performing its primary function, i.e., pumping liquid 31.

In FIGS. 2 and 3, volumetric pump 30 is illustrated in isometric view. As shown therein, volumetric pump 30 includes a molded plastic housing 70, having a handle 72 on its upper surface to facilitate carrying the volumetric pump to a point of use. A control panel 74 and a display 76 are disposed on the right side of the front surface of volumetric pump 30, and are respectively used by an operator for entry and display of data that controls the volumetric pump.

On the back of housing 70 is formed a clamp 88, which is used to removably attach volumetric pump 30 to a post 86, for example at the bedside of a patient. Details of clamp 88 are not shown, since it is generally typical of those used with other types of medical apparatus intended for connection to vertical posts.

In FIG. 2, door 78 is shown latched closed, the appropriate disposition for use of the volumetric pump, while in FIG. 3, door 78 is shown in an open position. A latch handle 80 is pivoted upwardly so that door 78 can be swung open on a hinge 96, giving access to an inner cover 92 that defines the path followed by flexible tubing 34 through volumetric pump 30. As noted above, when door 78 is opened while flexible tubing 34 is threaded through the volumetric pump and connected to container 32, free flow latch 38 clamps the flexible tubing closed to prevent liquid 31 in container 32 from free flowing through flexible tubing 34. The mechanism that actuates free flow latch 38 when door 78 is opened is not shown since it is not particularly relevant to the present invention.

Flexible tubing 34 is angled upwardly where it passes through an entry slot 82 formed on the side of door 78, insuring that any of liquid 31 leaking from container 32 drips from a loop formed in flexible tubing 34 and does not run into volumetric pump 30. After door 78 is swung open, flexible tubing 34 is readily threaded into a channel 90 defined along the longitudinal center of inner cover 92. An exit slot 84, formed in the lower side portion of door 78, overlies distal portion 34c of the flexible tubing. A pressure plate 94 disposed on the inner surface of door 78 comes into contact with flexible tubing 34 along the length of channel 90 as door 78 is closed and latched with handle 80.

FIGS. 4, 5, and 6 show details of the interior of volumetric pump 30. Pressure plate 94 defines a reference plane or surface in respect to each of the components of volumetric pump 30 that act to compress flexible tubing 34 and is mounted so that it floats on a plurality of helical coiled springs 212. Springs 212 bias pressure plate 94 away from the inner surface of door 78. When door 78 is closed, pressure plate 94 contacts inner cover 92 at several points. Helical springs 212, which are relatively stiff, are thus slightly compressed, and therefore accommodate variations in the tolerances of door 78 and other related parts that arise during construction of volumetric pump 30. Such tolerances might otherwise affect the position of the reference plane defined by pressure plate 94.

Most of the components comprising volumetric pump 30 are mounted on a frame 100 within housing 70. For example, frame 100 includes inlet cracking valve pivot mounts 102 and outlet cracking valve pivot mounts 104, about which inlet cracking valve 46 and outlet cracking valve 52 respectively pivot.

Inlet cracking valve 46 contacts proximal portion 34a of the flexible tubing along a valve face 106a. Similarly, outlet cracking valve 52 contacts distal portion 34c of the flexible tubing along a valve face 106b. The pivotal motion of inlet cracking valve 46 and outlet cracking valve 52 respectively varies the force with which valve faces 106a and 106b contact flexible tubing 34 to control fluid flow therethrough by compressing the flexible tubing against pressure plate 94. Plunger 48 compresses pumping portion 34b of the flexible tubing against pressure plate 94 to displace fluid from within a pumping chamber defined between the inlet and outlet cracking valves 46 and 52. In part because volumetric pump 30 includes inlet and outlet cracking valves 46 and 52, it operates differently than the prior art plunger type peristaltic pumps, as will be apparent from the following disclosure.

An inlet valve arm 108 extends upwardly from valve face 106a on inlet cracking valve 46. Disposed generally above inlet cracking valve pivot mounts 102 are flat metal spring flexures 110, which connect balance block 42 to a slot 134, formed on the back side of inlet valve arm 108. Flexures 110 are snapped within slot 134 and flex to enable inlet valve arm 108 to pivot valve face 106a away from pressure plate 94 through a greater angle than would otherwise be possible, without closing off fluid flow through flexible tubing 34 due to compression of the flexible tubing by balance block 42. Inlet cracking valve pivot mounts 102 are connected to downwardly depending pivot arms 136 on inlet cracking valve 46, at each side of flexible tubing 34, and are centered between balance block 42 and valve face 106a. The stiffness of flexible tubing 34 acts on balance block 42 and flexures 110, and the balance force developed as a function of this stiffness (or lack of elasticity) tends to pivot inlet valve face 106a against pressure plate 94, thereby increasing the force exerted by that part of inlet cracking valve 46 to compress the flexible tubing. The stiffness of flexible tubing 34 also resists compression by inlet valve face 106a to a similar extent. Accordingly, variations in the elasticity of flexible tubing 34 that affect the force required for inlet valve face 106a to compress the tubing are automatically compensated for by balance block 42.

Inlet cracking valve 46 operates in three distinct modes, the force applied by valve face 106a to compress flexible tubing 34 being substantially different in each mode. Two different spring-bias forces act on inlet valve arm 108. A fluid flow control force is applied to inlet valve arm 108 by a flat metal spring cracking flexure 112, acting against a knob 114, which is disposed at one end of inlet valve arm 108. The additional force necessary to compress flexible tubing 34 sufficiently to completely close off fluid flow past inlet cracking valve 46 is supplied by a flat metal spring closure flexure 120. Closure flexure 120 acts upon a side arm 116, disposed on one side of inlet valve arm 108. The combined force provided by cracking flexure 112 and closure flexure 120 (in addition to the balance force provided by balance block 42) pivots inlet cracking valve 46 about a pivot axis extending through inlet cracking valve pivot mounts 102, to completely block fluid flow through flexible tubing 34.

An inlet valve cam follower 122 selectively determines whether cracking flexure 112 and closure flexure 120 apply force against inlet valve arm 108 and thus determines the three modes in which inlet cracking valve 42 operates. Inlet valve cam follower 122 includes a roller 124 rotatably mounted in a hood 126, which is attached via an inlet follower flexure 128 to a plurality of blocks 130. Blocks 130 are also used in mounting cracking flexure 112 and closure flexure 120 to a bracket 135 and to provide appropriate spacing between these flexures and bracket 135. Bolts 132 connect the ends of each of these flexures to bracket 135, which comprises a portion of frame 100.

Roller 124 rolls along an inlet valve cam track 140, disposed on a rotating cam assembly 142. Cam assembly 142 turns on a camshaft 144, which at each of its ends is mounted to frame 100 in bearings 220 (see FIGS. 5 and 6). A motor shaft 148 extends downwardly from a motor 146, and a helical gear 224 on motor shaft 148 drivingly engages gear teeth 222, which are formed on one end of cam assembly 142, causing the cam assembly to rotate in a clockwise direction, as viewed in FIG. 4. The radial distance between camshaft 144 and the point where roller 124 contacts the surface of inlet valve cam track 140 varies as cam assembly 142 rotates, moving inlet valve cam follower 122 radially back and forth so as to control the forces applied to inlet valve arm 108. Specifically, as hood 126 is forced radially back against closure flexure 120, it lifts the closure flexure away from side arm 116, eliminating the force normally exerted by the closure flexure against the side arm and thereby reducing the total force exerted by valve face 106a against flexible tubing 34. In this configuration, inlet cracking valve 46 is in a "cracking mode."

As hood 126 moves further radially outward, closure flexure 120 contacts a "V-shaped" side arm 118 that is formed on the side of inlet valve arm 108, causing inlet valve arm 108 to pivot valve face 106a away from pressure plate 94. In this configuration, inlet cracking valve 46 is in an open mode, wherein liquid 31 freely flows from container 32 through proximal portion 34a of the flexible tubing and into pumping portion 34b. Flexures 110 bend as valve face 106a pivots away from pressure plate 94, so that balance block 42 does not close off fluid flow through proximal portion 34a of the flexible tubing.

When both closure flexure 120 and cracking flexure 112 are allowed to act on inlet valve arm 108, valve face 106a compresses flexible tubing 34 against pressure plate 94 sufficiently to completely block fluid flow through the flexible tubing. In this configuration, inlet cracking valve 46 is in a "closed mode."

An outlet valve cam track 150 is disposed between inlet valve cam track 140 and a plunger cam track 152. Plunger cam track 152 provides a surface at varying radii about camshaft 144 for actuating plunger 48 to compress pumping portion 34b of the flexible tubing against pressure plate 94. A roller 154 is rotatably mounted on a base 156 of plunger 48, and is thus disposed to roll along plunger cam track 152. Also mounted on base 156, at opposite sides of roller 154, are tubing shaper rollers 160. The disposition of tubing shaper rollers 160 is more clearly shown in FIGS. 5 and 6, and their operation in respect to shaping flexible tubing 34 is disclosed in detail below.

As shown using hidden lines in FIG. 4, the back side of cam assembly 142 includes a torque compensation track 170. A conically-shaped torque compensation roller 172 rolls along torque compensation track 170, applying a rotational torque to cam assembly 142 that compensates for an opposite torque resulting from rapid changes in the shape of inlet valve cam track 140, outlet valve cam track 150, and plunger cam track 152. Torque compensation roller 172 is mounted on a flat metal spring torque compensation flexure 174 that applies a biasing force to cam assembly 142.

Like inlet cracking valve 46, outlet cracking valve 52 has a generally "Y-shaped" configuration and includes an outlet valve arm 180, which is connected to outlet valve face 106b and to balance block 58. On opposite sides of flexible tubing 34, pivot arms 136 extend downwardly, connecting to outlet cracking valve pivot mounts 104 on frame 100. Balance block 58 rests on distal portion 34c of the flexible tubing and develops a force proportional to the stiffness (or lack of elasticity) of flexible tubing 34, which tends to increase the compression force applied against flexible tubing 34 by outlet valve face 106b to compensate or balance the resistance to compression caused by the stiffness (or lack of elasticity) of the flexible tubing. Just as balance block 42 compensates for changes or variations in elasticity of the flexible tubing in respect to inlet cracking valve 46, balance block 58 compensates for such changes and variations in respect to outlet cracking valve 52. However, since outlet cracking valve 52 is never pivoted to an open mode like inlet cracking valve 46, balance block 58 is integrally attached to outlet valve arm 180. Flexures 110 are not required, since the extent of pivotal rotation of outlet cracking valve 52 is substantially more limited than for inlet cracking valve 46. At all times, even when volumetric pump 30 is not pumping fluid, either inlet cracking valve 46 or outlet cracking valve 52 is in its closed mode, preventing liquid 31 from free flowing through flexible tubing 34.

As shown in FIG. 4, outlet cracking valve 52 is in its closed mode, compressing flexible tubing 34 against pressure plate 94 sufficiently to block fluid flow therethrough. In this configuration, a flat metal spring cracking flexure 182 applies force against a knob 184 on the top outlet valve arm 180. In addition, a flat metal spring closure flexure 188 applies a biasing force against a side arm 186 that extends outwardly from the side of outlet valve arm 180.

An outlet valve cam follower 190 includes a roller 192, which rolls along outlet valve cam track 150. Roller 192 is rotatably mounted within a hood 194, which is connected to a flat metal spring follower flexure 196. Follower flexure 196 spring biases roller 192 into contact with outlet valve cam track 150. The lower ends of follower flexure 196, cracking flexure 182, and closure flexure 188 are all secured at blocks 130 to bracket 135 by bolts 132, just as the corresponding elements are in respect to inlet cracking valve 46. As outlet valve cam follower 190 follows outlet valve cam track 150, hood 194 periodically contacts closure flexure 188, lifting it away from side arm 186 so that the flow control force provided by cracking flexure 182, added to the balance force developed by balance block 58, is transmitted to valve face 106b, thereby compressing flexible tubing 34 against pressure plate 94 with a cracking force. In this configuration, outlet cracking valve 52 is in its cracking mode.

As plunger 48 compresses pumping portion 34b of the flexible tubing against pressure plate 94, the pressure developed by liquid trapped between inlet cracking valve 46, which is closed, and outlet cracking valve 52 acts on valve face 106b, in opposition to the cracking force produced by cracking flexure 182 and balance block 58. As the force developed by the fluid pressure reaches a predetermined level sufficient to cause outlet cracking valve 52 to pivot open slightly, liquid 31 flows past the outlet cracking valve from pumping portion 34b of the flexible tubing. Liquid 31 is thus delivered by volumetric pump 30 at a predefined cracking pressure.

The first preferred embodiment of flow detector 54 comprises a strain gauge 198, which is mounted on cracking flexure 182. Strain gauge 198 develops an output signal corresponding to the stress developed in cracking flexure 182, and therefore indicates that outlet valve arm 180 is rotating to allow fluid flow past outlet cracking valve 52. Accordingly, strain gauge 198 determines whether fluid is being pumped through distal portion 34c of the flexible tubing as a result of displacement by plunger 48. If pumping portion 34b of the flexible tubing contains a relatively large proportion of air or other compressible gaseous fluid, plunger 48 cannot develop sufficient fluid pressure to overcome the cracking force exerted by cracking flexure 182 and balance block 58. As a result, strain gauge 198 fails to detect the stress of cracking flexure 182 that would have occurred if outlet valve arm 180 had pivoted open to allow fluid flow past outlet cracking valve 52 during a pumping stroke of plunger 48. Accordingly, the signal from strain gauge 198 is used to detect whether container 32 has run dry, allowing air to fill pumping portion 34b of the flexible tubing, or whether the flow of liquid 31 into volumetric pump 30 has otherwise been interrupted. The signal produced by strain gauge 198 is simply used as "go/no-go" signal as opposed to a signal that is accurately proportional to the movement of outlet valve arm 180. This go/no-go fluid flow detection signal is used to stop volumetric pump 30 and initiate an alarm when the expected fluid flow is not obtained, thereby alerting medical personnel of the problem so that it can be corrected.

Proximal pressure sensor 44 comprises a block 204, which is spring-biased into contact with proximal portion 34a of the flexible tubing and is disposed between inlet cracking valve 46 and balance block 42. A spring-bias force for proximal pressure sensor 44 is provided by two pairs of longitudinally extending flexures 202, disposed on each side of plunger 48. Flexures 202 are connected to support plates 266 on frame 100 by fasteners 206 at about the midpoint of the flexures. One of the four flexures 202 connecting block 204 to support plates 266 includes a strain gauge 200, which responds to stress developed in that flexure 202 as a function of fluid pressure within proximal portion 34a of the flexible tubing. As the fluid pressure increases within this portion of flexible tubing 34, flexures 202 connected to block 204 experience increased stress, producing a corresponding change in the output signal from strain gauge 200.

Similarly, distal pressure sensor 56 comprises a block 210, which is connected to the other ends of flexures 202. A strain gauge 208 is disposed on one of the four flexures, intermediate block 210 and one of the support plates 266. Strain gauge 208 produce a signal corresponding to the fluid pressure within distal portion 34c of the flexible tubing, based upon stress developed in flexures 202 as a result of that pressure. Distal pressure sensor 56 can be used to determine if distal portion 34c of the flexible tubing has been kinked, interrupting fluid flow through flexible tubing 34, for example, as might occur if a patient rolled over onto flexible tubing 34. Such a condition causes a notable increase in the distal fluid pressure that triggers an alarm and shuts off volumetric pump 30. If distal pressure sensor 56 should fail, flow detector 54 will also detect obstruction of fluid flow through distal portion 34c of the flexible tubing in response to cessation of fluid flow from volumetric pump 30.

In FIGS. 5, 6, and 7, details of tubing shapers 50a and 50b are disclosed. Since it is preferable to use relatively low cost PVC tubing in connection with volumetric pump 30, tubing shapers 50a and 50b are provided to ensure consistent operation and volumetric capacity of pumping portion 34b of the flexible tubing throughout the entire operating range of volumetric pump 30. At relatively high pumping rates, PVC tubing does not fully recover to its normal round uncompressed shape from a compressed condition rapidly enough to fill completely with fluid. Accordingly, the volumetric displacement of fluid within the PVC tubing that occurs with each pumping stroke is less than desired. To avoid this problem, tubing shapers 50a and 50b force pumping portion 34b of the flexible tubing to recover rapidly to its maximum volumetric capacity, i.e., to open sufficiently so that the desired amount of liquid 31 fills the pumping chamber defined by pumping portion 34b of the flexible tubing.

Each tubing shaper 50a and 50b comprises an angled arm 234, terminating at one end in a longitudinally extending jaw 236. Arms 234 are attached to frame 100 at pivot mounts 230, about which arms 234 rotate as tubing shaper rollers 160 roll along inner surfaces 232 of arms 234. Thus, the reciprocating up-and-down motion of plunger 48 along its reciprocation axis inherently acts on tubing shaper rollers 160 in "lock-step", causing jaws 236 to pinch pumping portion 34b of the flexible tubing at the proper time, thereby reforming flexible tubing 34 into the required pumping volume or capacity as plunger 48 lifts away from pressure plate 94.

In FIG. 5, tubing shapers 50a and 50b are shown moving in opposite directions, away from pumping portion 34b of the flexible tubing as plunger 48 descends to compress flexible tubing 34, displacing fluid from pumping portion 34b. However, in FIG. 6, plunger 48 is shown moving upwardly away from pressure plate 94, acting on tubing shaper rollers 160 to force opposing jaws 236 to swing inwardly toward each other in order to reshape pumping portion 34b of the flexible tubing so that it achieves its desired volumetric capacity.

To further enhance the repeatability and consistency of the volumetric capacity defined in pumping portion 34b of the flexible tubing, plunger cam track 152 is sized and shaped so that plunger 48 never completely compresses pumping portion 34b of the flexible tubing, even at the lowermost point of the plunger's reciprocal stroke. In addition, at the top of its reciprocal stroke, plunger 48 remains in contact with pumping portion 34b of the flexible tubing. The range of diametrical compression of flexible tubing 34 is from about 15% at the top of the pumping stroke to about 85% at the bottom of the pumping stroke of plunger 48. Since flexible tubing 34 need not recover to a fully uncompressed condition, i.e., to a perfect circular cross section, changes in the elasticity of flexible tubing 34 due to continued use and repeated compression have much less effect on the volumetric capacity of pumping portion 34b of the flexible tubing than would otherwise occur.

In order to calibrate tubing shapers 50a and 50b so that their range of motion corresponds to that required to achieve proper reshaping of pumping portion 34b of the flexible tubing, a wedge-shaped slot 240 is provided in the upper outer portion of arms 234. To adjust the angle between the upper and lower portions of portions of each arm 234, a wedge-shaped insert 238 is driven into wedge-shaped slot 240, deflecting the upper portion of arm 234 through an angle, as indicated by reference numeral 242. Angle 242 is determined by use of an appropriate calibration jig (not shown) during manufacture of tubing shapers 50a and 50b, or during assembly of these components in volumetric pump 30.

Figure 9:
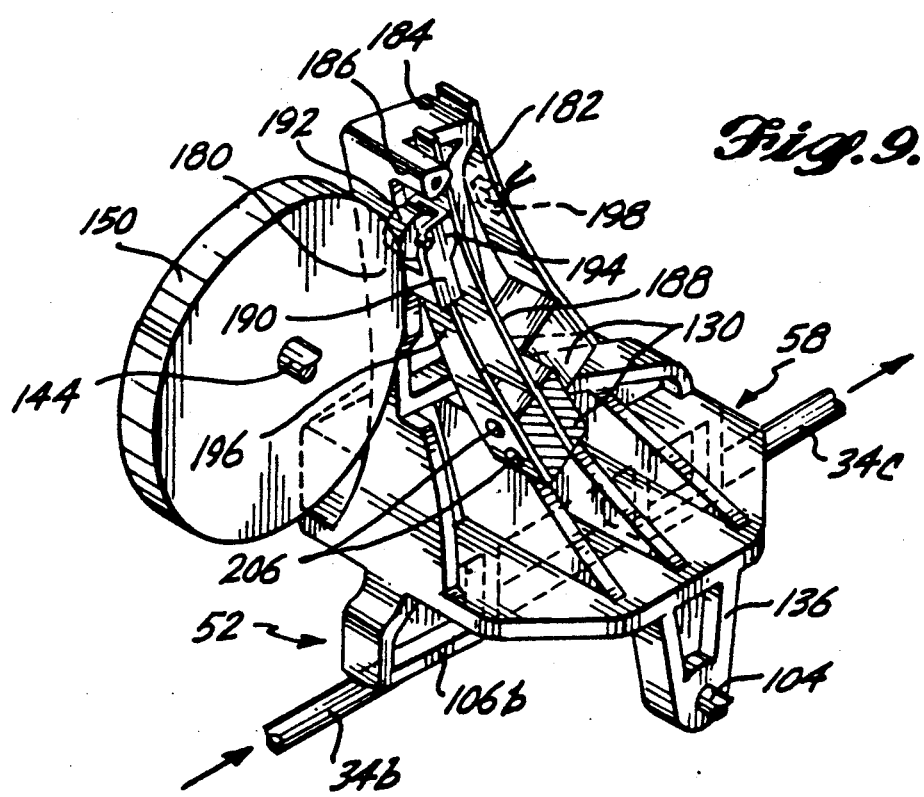
FIG. 9 is an analogous view to that of FIG. 8, isometrically showing an outlet cracking valve used in the volumetric pump and a transverse section of the cam assembly that is used to actuate the outlet cracking valve, and also showing how a first embodiment of a sensor used in the present invention is disposed to detect fluid flow past the outlet cracking valve.
Figure 10A:
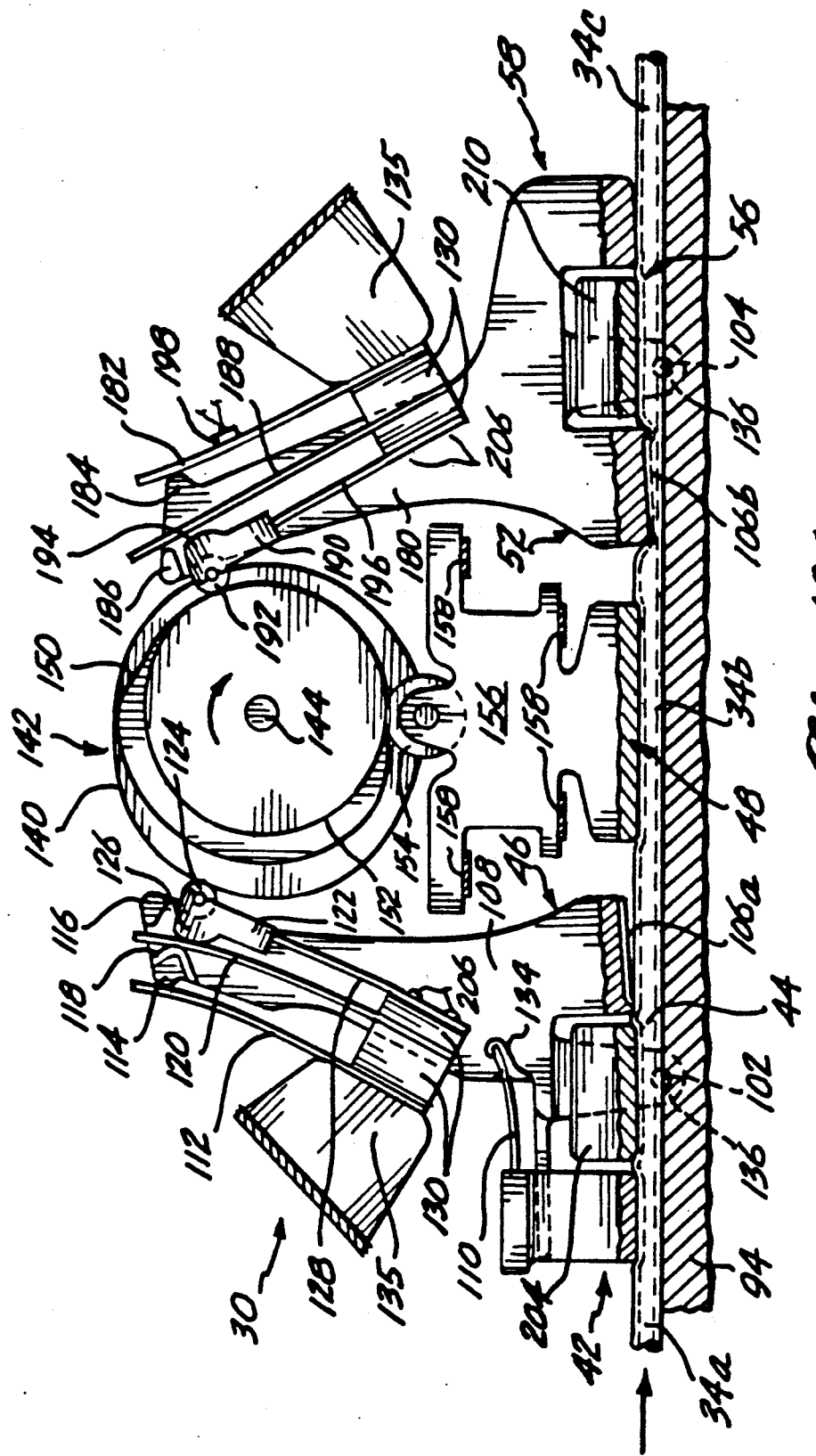
Figure 10C:
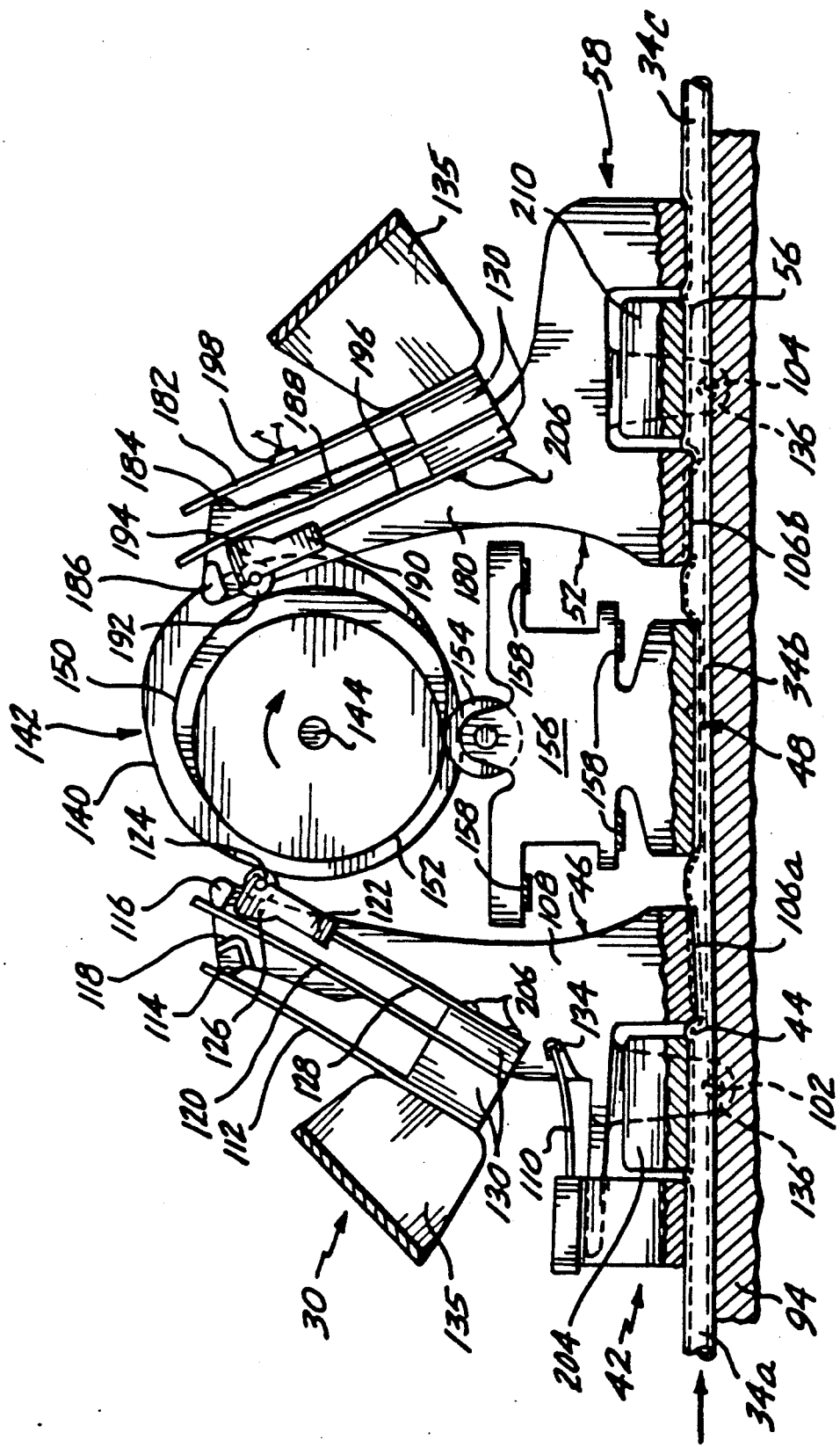

Details of inlet cracking valve 46 are shown in FIG. 8, and details of outlet cracking valve 52 are shown in FIG. 9. In these drawings, it is apparent that downwardly depending pivot arms 136 straddle flexible tubing 34, and are spaced apart sufficiently so that blocks 204 and 210 of proximal pressure sensor 44 and distal pressure sensor 56 can fit therebetween. FIG. 8 more clearly illustrates side arm 116 and V-shaped side arm 118 at the top of inlet valve arm 108. In FIG. 9, the specific disposition of side arm 186 in respect to outlet valve cam follower 190, closure flexure 188, and cracking flexure 182 is also more clearly shown.

One of the advantages of using flat metal spring flexures, i.e., cracking flexure 112 and closure flexure 120, for biasing inlet valve arm 108 is that the force provided by each of these flexures is much more readily controlled than is typically the case with other types of spring assemblies. For example, by trimming the shape of these flexures or selecting flexures of a different thickness, the spring force they produce (i.e., their spring constant, K) can be readily modified and consistently controlled. The same advantages apply to the other flexures used in volumetric pump 30, such as inlet follower flexure 128 and balance block flexures 110. Accordingly, the cracking pressure and other characteristics of volumetric pump 30 can be precisely determined.

Figure 11:
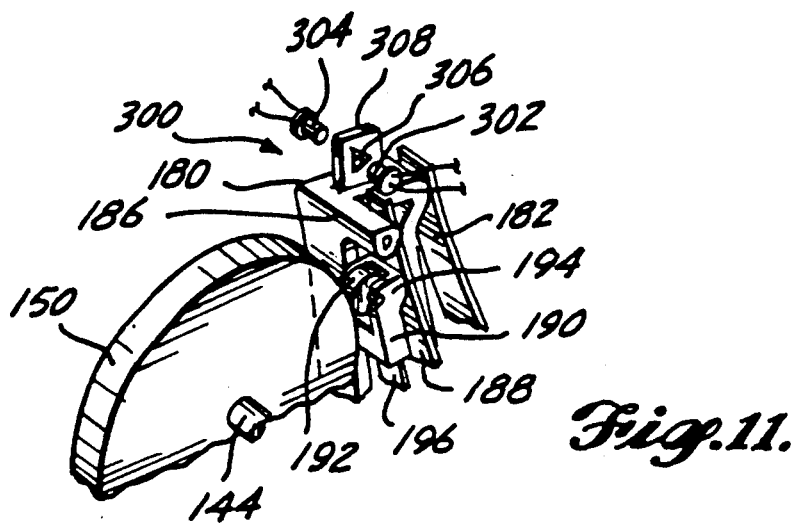
FIG. 11 illustrates a second embodiment of the sensor used in the present invention and shows a portion of the outlet cracking valve arm.

Instead of using strain gauge 198 to sense stress in cracking flexure 182 as outlet cracking valve 52 opens, other types of sensors may be mounted proximal outlet valve arm 180 to produce a signal indicative of its pivotal motion. For example, the pivotal movement of outlet valve arm 180 as fluid flows past outlet cracking valve 52 can be detected using an optical sensor 300, as shown in FIG. 11. To accommodate optical sensor 300, the upper end of outlet valve arm 180 is modified to include a tab 308. Centered within tab 308 is a triangular shaped aperture 306. Disposed on opposite sides of tab 308 are a light emitting diode (LED) 302 and a phototransistor 304. Light emitted by LED 302 passes through triangular shaped aperture 306 and is picked up by phototransistor 304. When outlet cracking valve 52 is closed, only a very small portion of phototransistor 304 is illuminated by light from LED 302 through the apex of triangular shaped aperture 306. However, as outlet valve arm 180 moves because of fluid flow past outlet cracking valve 52, the amount of light emitted by LED 302 that reaches phototransistor 304 increases, since the light can pass through the larger area of triangular shaped aperture 306 adjacent its base. Accordingly, the signal produced by phototransistor 304 serves to indicate whether outlet valve arm 180 has moved to permit fluid flow from volumetric pump 30.

Figure 12:
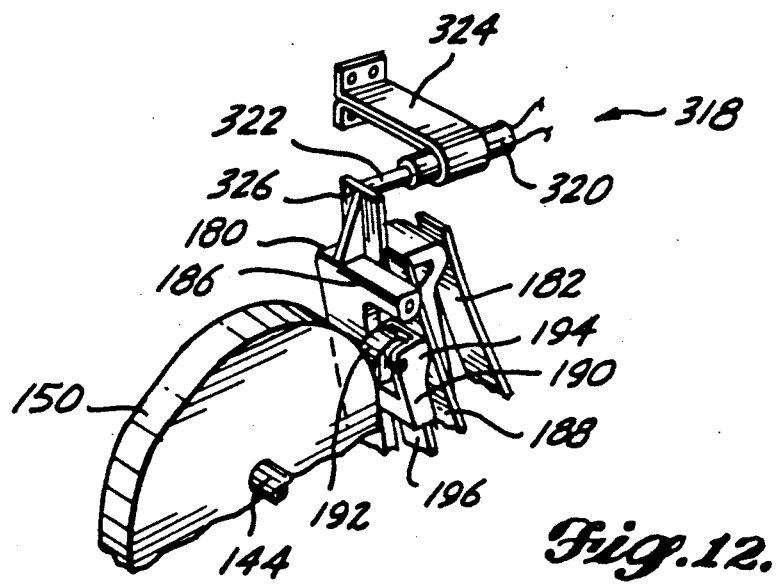
FIG. 12 illustrates a third embodiment of the sensor used in the present invention and a portion of the outlet cracking valve arm.

In FIG. 12, a linear variable displacement transformer (LVDT) 318 is used to detect whether outlet valve arm 180 has moved to allow fluid flow from volumetric pump 30 past outlet cracking valve 52. In this embodiment, the upper end of outlet valve arm 180 is modified to include a transverse tab 326. Tab 326 abuts against a ferrous metal core 322, which extends from the center LVDT 318. LVDT 318 also comprises a plurality of electro-magnetic coils 320 including a primary coil and two secondary coils (not separately shown). As ferrous metal core 322 is forced further into electro-magnetic coils 320 by tab 326 as outlet cracking valve 52 opens, the ferrous metal core increases the extent of magnetic coupling between the electro-magnetic coils, changing the signal LVDT 318 produces. A bracket 324 supports electro-magnetic coils 320 at a fixed position with respect to the movement of ferrous metal core 322. A helical coil spring (not shown) inside LVDT 318 biases ferrous magnetic core 322 into contact with tab 326.

It is also contemplated that a Hall sensor could be mounted adjacent outlet valve arm 180 to detect the motion of a magnet bonded to the outlet valve arm, as outlet cracking valve 52 opens to enable fluid flow from volumetric pump 30. In addition, flow detector 54 may also comprise a variable capacitor that changes capacitance value as outlet valve arm 180 pivots. LVDT 318 and a variable capacitor are simply different types of variable reactance sensors. Clearly, those of ordinary skill in the art will recognize that these and other types of sensors for detecting motion of outlet valve arm 180 can serve as an indication of fluid flow from volumetric pump 30.

Figure 13:
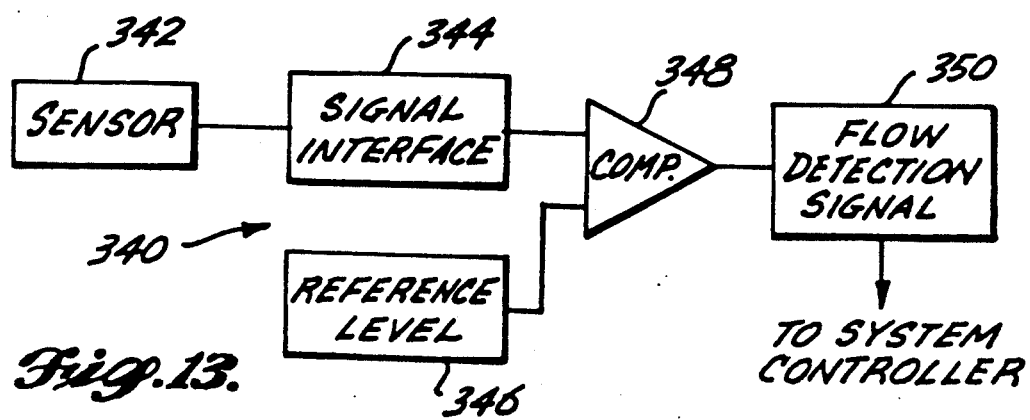
FIG. 13 is a schematic block diagram of a circuit used in connection with the sensor for detecting fluid flow from the volumetric pump; and, FIG. 14 is a schematic block diagram illustrating a volumetric pump controller that is responsive to a signal output from the sensor circuit of FIG. 13.

FIG. 13 illustrates a circuit 340 that is used in connection with strain gauge 198, optical sensor 300, LVDT 318, or with the alternative sensors that can comprise flow detector 54 (as discussed above) to produce a signal indicative of movement of outlet valve arm 180 and thus indicative of fluid flow from volumetric pump 30. As shown in FIG. 13, a sensor block 342 produces a signal indicating whether outlet valve arm 180 has moved to enable fluid flow from the volumetric pump. The signal produced by the sensor in block 342 is input to a signal interface 344. The function performed by interface 344 depends upon the type of sensor used to monitor the motion of outlet valve arm 180. For example, if optical sensor 300 is employed, signal interface 344 comprises a simple amplifier used to amplify the signal from photo transistor However, if LVDT 318 is employed, signal interface 344 comprises a differential amplifier that produces a signal indicative of the difference in electromagnetic coupling between the primary coil and two secondary coils comprising electro-magnetic coils 320 as ferrous metal core 322 is moved into the center of the LVDT.

A signal output from signal interface 344 comprises an analog DC level that is input to a comparator block 348, for comparison to a reference analog signal produced in block 346. If, for example, the signal output from signal interface block 344 exceeds the reference signal level from reference block 346, comparator 348 generates a logic level signal indicating that outlet valve arm 180 has moved the required distance representative of fluid flow from volumetric pump 30. Thus the logic signal from comparator 348 is a flow detection signal, as shown in block 350, which is input to a system controller 280 shown in FIG. 14.

Figure 14:
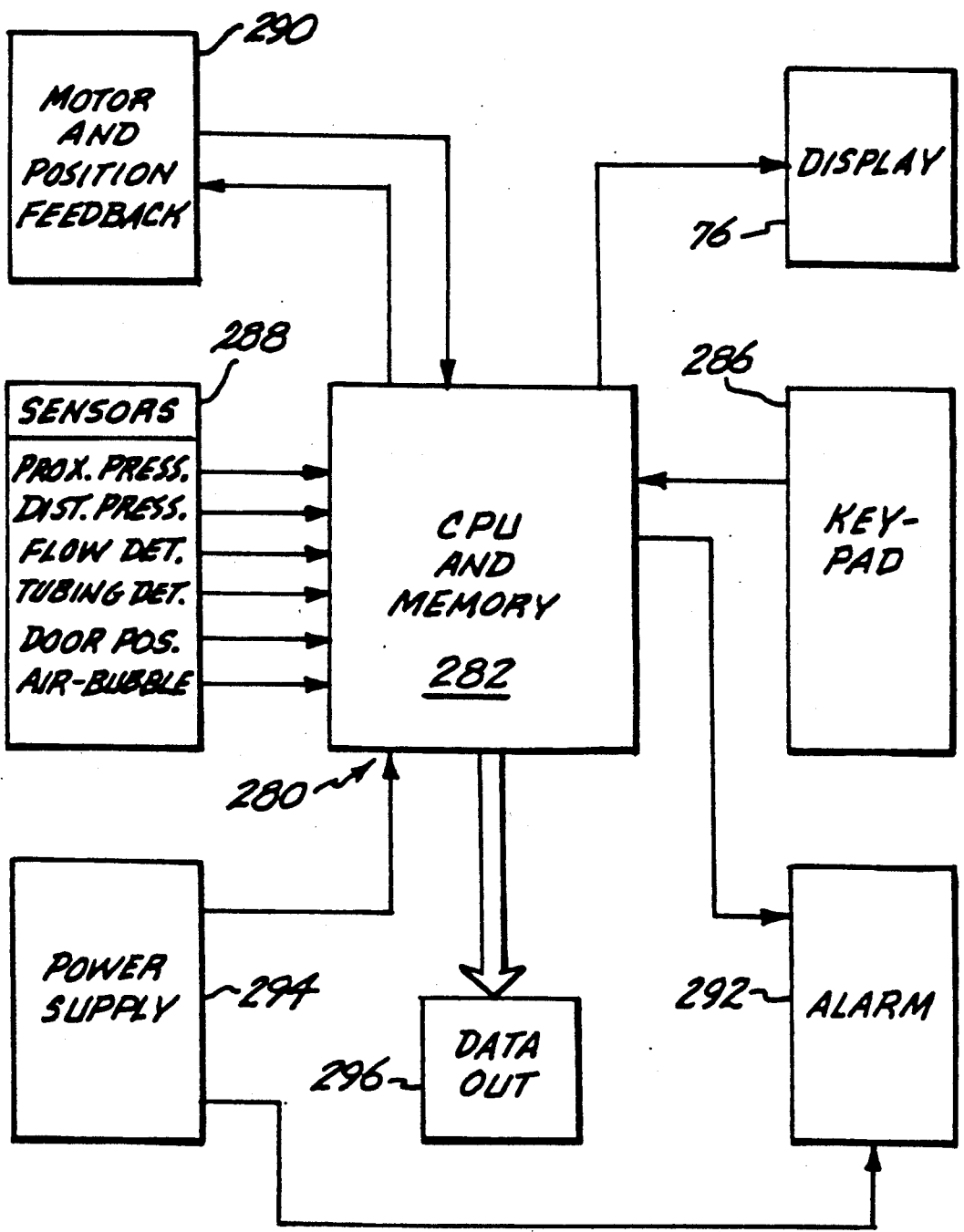

Turning now to FIG. 14, it is apparent that system controller 280 includes a microprocessor CPU and memory block 282. Software algorithms that control volumetric pump 30 are implemented within the CPU in response to input control data provided by an operator on a keypad 286. For example, an operator might enter specific times during which volumetric pump 30 should administer a prescribed volume of liquid 31 intravenously to a patient, at a prescribed flow rate. The control data entered via keypad 286 are shown on display 76.

In accordance with the control data entered on keypad 286, CPU and memory block 282 actuates the motor at the required time, controls it to administer the prescribed volume of liquid 31 at the prescribed rate, and keeps track of its progress through the pumping cycle in respect to signals provided by various sensors on volumetric pump 30 to detect problems that may affect the performance of the volumetric pump. For example, if flow detector 54 fails to produce a signal indicating that fluid has forced open outlet cracking valve 52 as plunger 48 has completed a pumping segment of the pumping cycle, the CPU causes both a visual and audio audible signal to be generated by an alarm 292, to alert medical personnel that volumetric pump 30 has ceased pumping liquid 31 to the patient. Similarly, in the event that any of the other signals provided by the sensors in block 288 indicate a potentially harmful fault condition, such as an air bubble in the fluid within distal portion 34c of the flexible tubing, an alarm is also generated. For purposes of recording patient history and to interface with other controllers, a data output path 296 is optionally provided for CPU and memory block 282. A power supply 294 provides power for CPU and memory block 282 and for alarm 292.

Although the present invention has been disclosed in respect to a preferred embodiment and modifications thereto, those of ordinary skill in the art will appreciate that further modifications may be made to the present invention within the scope of the claims that follow. Accordingly, it is not intended that the scope of the invention be in any way limited by the disclosure of the preferred embodiment, but that it be entirely determined by reference to the claims.

The embodiments of the invention in which an exclusive property or privilege is claimed are defined as follows:

1. Apparatus for sensing fluid flow through a passage defined by a flexible member in a positive displacement pump, comprising:
   a. a valve member, mounted in the pump to pivot around a pivot axis, said valve member including a surface that engages the flexible member;
   b. a spring mounted in biasing relationship to the valve member, causing the valve member to pivot around the pivot axis so that the valve member compresses a portion of the flexible member with a cracking force, restricting fluid flow through the passage, a fluid pressure in the passage in excess of a predetermined cracking pressure producing a force that opposes the cracking force developed by the spring, enabling fluid to flow through the passage past the valve member;
   c. flow detector means, mounted proximal the spring, for producing a signal indicative of deflection experienced by the spring due to fluid pressure acting on the valve member in opposition to the cracking force developed by the spring; and d. control means, connected to receive the signal produced by the flow detector means, for determining whether fluid is flowing past the valve member within the passage as a function of said signal.

2. The apparatus of claim 1, wherein the fluid pressure developed as the pump attempts to positively displace a gaseous fluid within the passage is less than the cracking pressure and cannot enable the gaseous fluid to flow past the valve member.

3. The apparatus of claim 2, wherein the control means are operative to determine whether the pump is compressing the gaseous fluid or positively displacing a liquid, as a function of said signal.

4. The apparatus of claim 1, wherein the flexible member comprises flexible tubing through which the fluid flows, and the valve member compresses the flexible tubing against a backing surface on the pump to restrict fluid flow through the pump past the valve member.

5. The apparatus of claim 1, wherein the spring comprises an elongate flat flexure that is mounted at one point along its length to the pump and extends therefrom into abutting contact with the valve member.

6. The apparatus of claim 5, wherein the valve member includes a surface against which the flexure abuts to apply the force biasing the valve member to compress the flexible member.

7. The apparatus of claim 6, wherein said flow detector means are disposed between said point where the flexure is mounted to the pump and a point where the flexure abuts against the surface of the valve member.

8. The apparatus of claim 1; wherein the control means determine that the fluid is flowing past the valve member if a magnitude of the signal produced by the flow detector means exceeds a predetermined level.

9. The apparatus of claim 1, wherein the flow detector means comprise a strain gauge that is attached to the spring and produces said signal in response to the stress that the spring experiences as a result of movement of the valve member.

10. The apparatus of claim 1, wherein the flow detector means comprise an optical sensor.

11. The apparatus of claim 1, wherein the flow detector means comprise a Hall effect sensor.

12. The apparatus of claim 1, wherein the flow detector means comprise a variable reactance sensor.

13. A fluid flow detector for determining that a fluid is flowing out of an outlet port of a positive displacement pump as the pump compresses flexible tubing to displace fluid from within a pumping portion of the flexible tubing, comprising:

a. an outlet valve member, mounted in the pump to pivot about a pivot axis into contact with the flexible tubing;

b. spring bias means for applying a cracking force against the outlet valve member, causing it to pivot about the pivot axis, compressing the flexible tubing against a backing plate and thereby restricting fluid flow through the outlet port until a fluid pressure within the pumping portion of the flexible tubing produces a force that acts on the outlet valve member, enabling fluid to flow past the outlet valve member and through the outlet port of the pump; and c. a flow sensor, disposed proximate to the spring bias means, and operative to monitor the deflection of the outlet valve member caused by fluid pressure in the flexible tubing, and in response thereto, operative to produce a signal indicative of whether the pressure within the pumping portion of the flexible tubing is producing a force acting on the outlet valve member in excess of the cracking force, thereby causing the outlet valve member to open, and enabling fluid flow from the pump.

14. The fluid flow detector of claim 13, wherein the pressure developed within the pumping portion of the flexible tubing by the pump compressing a gaseous fluid is always less than that required to produce a force in excess of the cracking force, so that compressed gaseous fluid cannot flow past the outlet valve member and out of the pump.

15. The fluid flow detector of claim 14, wherein the deflection sensor is further operative to detect whether a liquid is being positively displaced or a gaseous fluid is being compressed in the pumping portion of the flexible tubing, since the gaseous fluid does not develop sufficient pressure to force open the outlet valve member.

16. The fluid flow detector of claim 13, wherein the spring bias means comprise an elongate flat flexure that is mounted on the pump and abuts against the outlet valve member.

17. The fluid flow detector of claim 16, wherein the deflection sensor comprises a strain gauge attached to the flexure, which produces the signal, said signal being proportional to a stress applied by the outlet valve member to deflect the flexure.

18. The fluid flow detector of claim 16, wherein the deflection sensor is disposed on the flexure intermediate a point where the flexure is mounted to the pump and a point where it abuts the outlet valve member.

19. The fluid flow detector of claim 13, wherein the deflection sensor comprises an optical sensor.

20. The fluid flow detector of claim 13, wherein the deflection sensor comprises a Hall effect sensor.

21. The fluid flow detector of claim 13, wherein the deflection sensor comprises a variable reactance sensor.

22. The fluid flow detector of claim 13, wherein the outlet valve member comprises an actuator portion acted upon by the spring bias means and a flow control portion connected to the actuator portion, which compresses the flexible tube to control fluid flow therethrough due to the cracking force applied by the spring bias means against the actuator portion.

* * * * *